(12) United States Patent
Liu et al.

(10) Patent No.: US 12,406,090 B2
(45) Date of Patent: Sep. 2, 2025

(54) DATA MANAGEMENT SYSTEM TO TRACK AND DISTRIBUTE PUBLIC DATA COLLECTION WITH USER PRIVACY PROTECTION AND EVENT TOKEN EXCHANGE

(71) Applicant: HUAWEI TECHNOLOGIES CO., LTD., Shenzhen (CN)

(72) Inventors: Lifeng Liu, Sudbury, MA (US); Jian Li, Waltham, MA (US)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 254 days.

(21) Appl. No.: 18/177,012

(22) Filed: Mar. 1, 2023

(65) Prior Publication Data

US 2023/0205928 A1 Jun. 29, 2023

Related U.S. Application Data

(63) Continuation of application No. PCT/US2020/049078, filed on Sep. 2, 2020.

(51) Int. Cl.
*G06F 21/62* (2013.01)
*G16H 40/67* (2018.01)
*G16H 50/80* (2018.01)

(52) U.S. Cl.
CPC ......... *G06F 21/6245* (2013.01); *G16H 40/67* (2018.01); *G16H 50/80* (2018.01)

(58) Field of Classification Search
CPC .... G06F 21/4625; G16H 40/67; G16H 50/80; G16H 10/60
See application file for complete search history.

(56) References Cited

U.S. PATENT DOCUMENTS

2013/0318027 A1* 11/2013 Almogy ................. G16H 50/20
706/52
2017/0206334 A1 7/2017 Huang
2018/0052970 A1* 2/2018 Boss ....................... G06F 21/35

OTHER PUBLICATIONS

Sun, Ruoxi, et al. "Vetting security and privacy of global covid-19 contact tracing applications." arXiv preprint arXiv:2006. 10933. Jul. 2020.*

(Continued)

*Primary Examiner* — John M Macilwinen

(57) ABSTRACT

A data management system for collecting data of users from sensors at an event. An event-specific token corresponding to the event attended by the users is generated, where the event-specific token includes event-specific signatures about the users attending the event, and the signature of the event venue or facility. The public data is sent to public storage as an aggregation of the collected data and tagged with the event-specific token. The public data is statistically analyzed to track interactions and assess risks of the user's potential infection of a communicable disease based on anomalous activity detected at the event, or based on the notifications from the event attendees, which are matched and validated anonymously using the event-specific tokens. Based on a result of the statistical analysis, an advisory alert is sent to the users to warn them of a level of risk of harm based on attendance of the event.

20 Claims, 7 Drawing Sheets

(56) References Cited

OTHER PUBLICATIONS

Hay, Simon, and Robert Harle. "Bluetooth tracking without discoverability." International Symposium on Location-and Context-Awareness. Berlin, Heidelberg: Springer Berlin Heidelberg. (Year: 2009).*
Cho, Hyunghoon, Daphne Ippolito, and Yun William Yu. "Contact tracing mobile apps for COVID-19: Privacy considerations and related trade-offs." arXiv preprint arXiv:2003.11511. Mar. 2020.*
Troncoso, Carmela, et al. "Decentralized privacy-preserving proximity tracing." arXiv preprint arXiv:2005.12273. May 2020.*
Trieu, Ni, et al. "Epione: Lightweight contact tracing with strong privacy." arXiv preprint arXiv:2004.13293. May 2020.*
Altuwaiyan, Thamer, Mohammad Hadian, and Xiaohui Liang. "EPIC: efficient privacy-preserving contact tracing for infection detection." 2018 IEEE International Conference on Communications (ICC). IEEE. (Year: 2018).*
Ahmed, Nadeem, et al. "A survey of COVID-19 contact tracing apps." IEEE access 8:134577-134601. Jul. 2020.*
International Preliminary Report on Patentability dated Mar. 16, 2023, International Application No. PCT/US2020/049078.
International Search Report and Written Opinion dated May 19, 2021, International Application No. PCT/US2020/049078.
Ruoxi, Sun et al., "Vetting Security and Privacy of Global COVID-19 Contact Tracing Applications", Jul. 22, 2020, pp. 1-13.
Trieu, Ni et al., "Epione: Lightweight Contact Tracing with Strong Privacy", May 2, 2020, pp. 1-32.

* cited by examiner

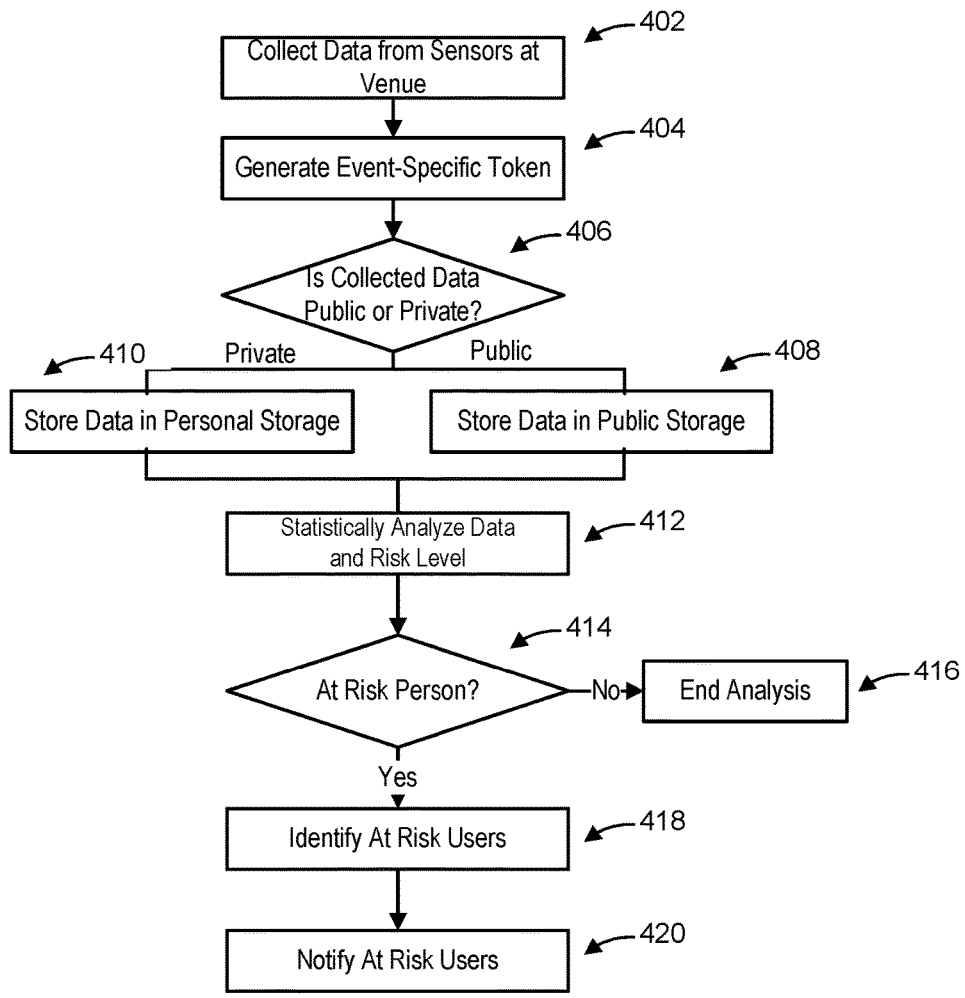

Block 802

Date, time period. Hash value of the block

Merklee tree of events (recording passengers' health measurements):

Traveling trajectory:
{
  {timestamp, location/Place ID}
  ......
}

Event1: {
  Event token;
  userID;
  timestampOfEntering;
  timestampOfLeaving;
  Health measurements {
    (value1, deviceID1, ......);
    ......
  };
  Other passengers with close contact {
    { pseudo user ID1;
      estimated closest distance;
      durationTime;
    }
    ......
  }// other passengers
}//Event1
......

Block 804

Date, time period. Hash value of the block

Merklee tree of events (recording visitors' health measurements):

Event1: {
  Event token;
  pseudo userID;
  timestampOfEntering;
  timestampOfLeaving;
  Health measurements {
    (value1, deviceID1, ......);
    ......
  };
  Other Visitors with close contact {
    { pseudo user ID1;
      estimated closest distance;
      durationTime;
    }
    ......
  }// other visitors
}//Event1
......

Block 806

Date, time period. Hash value of the block

Merklee tree of events (recording traveling trajectory and health measurements):

Event1: {
  timestamp;
  location and PlaceID;
  Health measurements {
    (value1, deviceID1, ......);
    ......
  };
  Contacts {
    Contact1 {
      event token;
      estimated closest distance;
      durationTime;
    }
    ......
  }// Contacts
}//Event1
......

*FIG. 8B*

DATA MANAGEMENT SYSTEM TO TRACK AND DISTRIBUTE PUBLIC DATA COLLECTION WITH USER PRIVACY PROTECTION AND EVENT TOKEN EXCHANGE

CLAIM OF PRIORITY

This application is a continuation of, and claims priority to, PCT Patent Application No. PCT/US2020/049078, entitled "DATA MANAGEMENT SYSTEM TO TRACK AND DISTRIBUTE PUBLIC DATA COLLECTION WITH USER PRIVACY PROTECTION AND EVENT TOKEN EXCHANGE", filed Sep. 2, 2020, which application is incorporated by reference herein in its entirety.

FIELD

The disclosure generally relates to data collection, analysis and management, and in particular, to controlling the spread of communicable diseases while maintaining the privacy of user information.

BACKGROUND

Tracking and analyzing the spread of disease and infection presents challenges. In many locations, collecting and tracking disease and infection information is not only challenging, but also presents difficulty in quickly communicating the information to people to prevent further spread of disease and infection. Earlier detection of a disease and infection outbreak offers the best opportunity to mitigate its effects. Accordingly, one of the core functions of public health management is to monitor public health status and identify disease and infection information as soon as possible, as well as notify the public of any such incidence or occurrence of the information. Early intervention allows for early recognition of affected individuals, initiation of treatment, and initiation of post-exposure mitigations among the exposed population.

SUMMARY

According to one aspect of the present disclosure, there is a computer-implemented method for managing data in a network, comprising collecting data of an event, at a platform having one or more processors, of one or more users from a plurality of sensors located in the network, the sensors including personal monitoring devices and public monitoring devices; generating, by the one or more processors of the platform, an event-specific token corresponding to the event attended by the one or more users, the event-specific token including event-specific signatures about the one or more users attending the event; sending public data, by the platform via the network, for storage to a public storage as an aggregation of the collected data of the one or more users, the public data of the one or more users collected using the public monitoring devices and tagged with the event-specific token; statistically analyzing the public data, by the one or more processors of the platform, collected from the plurality of sensors at the event to track interactions and assess risks of the one or more user's potential infection of a communicable disease based on anomalous activity detected at the event; and sending an advisory alert, by the platform via the network, to the one or more users personal monitoring device based on a result of the statistical analysis to warn the one or more users of a level of risk of harm based on attendance of the event, each of the one or more user's personal monitoring device analyzing the event-specific token to identify a relevance of the advisory alert to each of the one or more users.

Optionally, in any of the preceding aspects, the method further comprising receiving, via the network, personalized data of each of the one or more users from a corresponding private storage, the personalized data of each of the one or more users collected using the plurality of sensors and tagged with the event-specific token, wherein the public data includes the personalized data for the statistical analysis when the one or more users authorize sharing the corresponding personalized data, the personalized data maintaining the anonymity of the one or more users in the public storage by removing user identities and matching the event-specific token of the personalized data with the event-specific token of the public data.

Optionally, in any of the preceding aspects, the aggregation includes clustering the aggregated public data and the personalized data to identify clusters of data grouped according to defined categories of information.

Optionally, in any of the preceding aspects, the aggregated public data and the personalized data include the collected data that satisfies one or more conditions or thresholds.

Optionally, in any of the preceding aspects, the method further comprising receiving, via the network, a notification from the personal monitoring device of one of the users previously in attendance of the event that indicates the user has been infected with the communicable disease, the notification including a copy of the event-specific token and an event-specific signature from the one or more users; and validating, by the one or more processors of the platform, the notification sent by the personal monitoring device by comparing the event-specific signature of the one or more users to signatures of the one or more users stored in the public storage.

Optionally, in any of the preceding aspects, the event-specific signature is generated for the event using a private key.

Optionally, in any of the preceding aspects, statistical analysis by the one or more processors of the platform comprises one or more of measuring how many of the one or more users in attendance at the event have been in close proximity to one another; determining how many of the one or more users are infected by a same communicable disease; and predicting the spread of the communicable disease based on transportation and mobility patterns and restrictions placed on the transportation and mobility of the one or more users subsequent to attendance at the event.

Optionally, in any of the preceding aspects, the method further comprising distributing, by the platform, the event-specific token to the personal monitoring device and the public monitoring devices in the network, wherein the event-specific token distributed to the personal monitoring device includes an event hosting facility identifier, a device identifier, a time stamp, an event identifier, a number of the one or more users, the collected data from the plurality of sensors, signatures of the event hosting facility and an event-specific user key, and the event-specific token distributed to the public monitoring device includes the event hosting facility identifier, the device identifier as the anonymous identifying information, the time stamp, the event identifier, the number of the one or more users, the collected data from the plurality of sensors, the event-specific signatures of the one or more users and an event hosting facility key.

Optionally, in any of the preceding aspects, the method further comprising exchanging, by the platform, the signature of the one or more users with the signature of the event hosting facility during distribution of the event-specific token to the personalize monitoring device and the public monitoring device, wherein the signature of the one or more users is generated using the user key, and the signature of the event hosting facility is generated using the event hosting facility key.

Optionally, in any of the preceding aspects, the method further comprising receiving, by the platform, a new signature of the one or more users generated by the personal monitoring device, the new signature generated using a newly generated key; and updating, by the platform, the event-specific token of the public data with the new signature.

Optionally, in any of the preceding aspects, the event hosting facility identifier and the device identifier is one of a pseudo identifier or a geographic identifier.

Optionally, in any of the preceding aspects, the event-specific token distributed to the personal monitoring device of the one or more users includes the signature of the event hosting facility to validate the event-specific token upon receipt of the advisory alert.

Optionally, in any of the preceding aspects, the collected data is tracing data used to trace the one or more users in attendance at the event.

Optionally, in any of the preceding aspects the collected data is stored as a hierarchical graph structure linking, via the event-specific tokens, groups of the one or more users based on the clustering of the aggregated public data and the personalized data.

According to one other aspect of the present disclosure, there is provided an apparatus for data management, comprising a non-transitory memory storage comprising instructions; and one or more processors in communication with the memory, wherein the one or more processors execute the instructions to collect data of an event, via the network, of one or more users from a plurality of sensors located in the network, the sensors including personal monitoring devices and public monitoring devices; generate an event-specific token corresponding to the event attended by the one or more users, the event-specific token including event-specific signatures about the one or more users attending the event; send public data, via the network, for storage to a public storage as an aggregation of the collected data of the one or more users, the public data of the one or more users collected using the public monitoring devices and tagged with the event-specific token; statistically analyze the public data collected from the plurality of sensors at the event to track interactions and assess risks of the one or more user's potential infection of a communicable disease based on anomalous activity detected at the event; and send an advisory alert, via the network, to the one or more users personal monitoring device based on a result of the statistical analysis to warn the one or more users of a level of risk of harm based on attendance of the event, the event-specific token analyzed to identify a relevance of the advisory alert to each of the one or more users.

According to still one other aspect of the present disclosure, there is a non-transitory computer-readable medium storing computer instructions for data management, that when executed by one or more processors, cause the one or more processors to perform the steps of collecting data of an event of one or more users from a plurality of sensors located in the network, the sensors including personal monitoring devices and public monitoring devices; generating an event-specific token corresponding to the event attended by the one or more users, the event-specific token including event-specific signatures about the one or more users attending the event; sending public data, via the network, for storage to a public storage as an aggregation of the collected data of the one or more users, the public data of the one or more users collected using the public monitoring devices and tagged with the event-specific token; statistically analyzing the public data collected from the plurality of sensors at the event to track interactions and assess risks of the one or more user's potential infection of a communicable disease based on anomalous activity detected at the event; and sending an advisory alert, via the network, to the one or more users personal monitoring device based on a result of the statistical analysis to warn the one or more users of a level of risk of harm based on attendance of the event, the event-specific token analyzed to identify a relevance of the advisory alert to each of the one or more users.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the Background.

BRIEF DESCRIPTION OF THE DRAWINGS

Aspects of the present disclosure are illustrated by way of example and are not limited by the accompanying figures for which like references indicate elements.

FIG. 4 illustrates an example flow diagram for collecting and analyzing data for contact tracing.

FIG. 5A illustrates an event-specific token for storage in a public health database.

FIG. 5B illustrates an event-specific token for storage in a personal health database.

FIGS. 8A and 8B illustrate an example graph structure linking individuals and facilities using blockchain technology.

DETAILED DESCRIPTION

Figure 1:
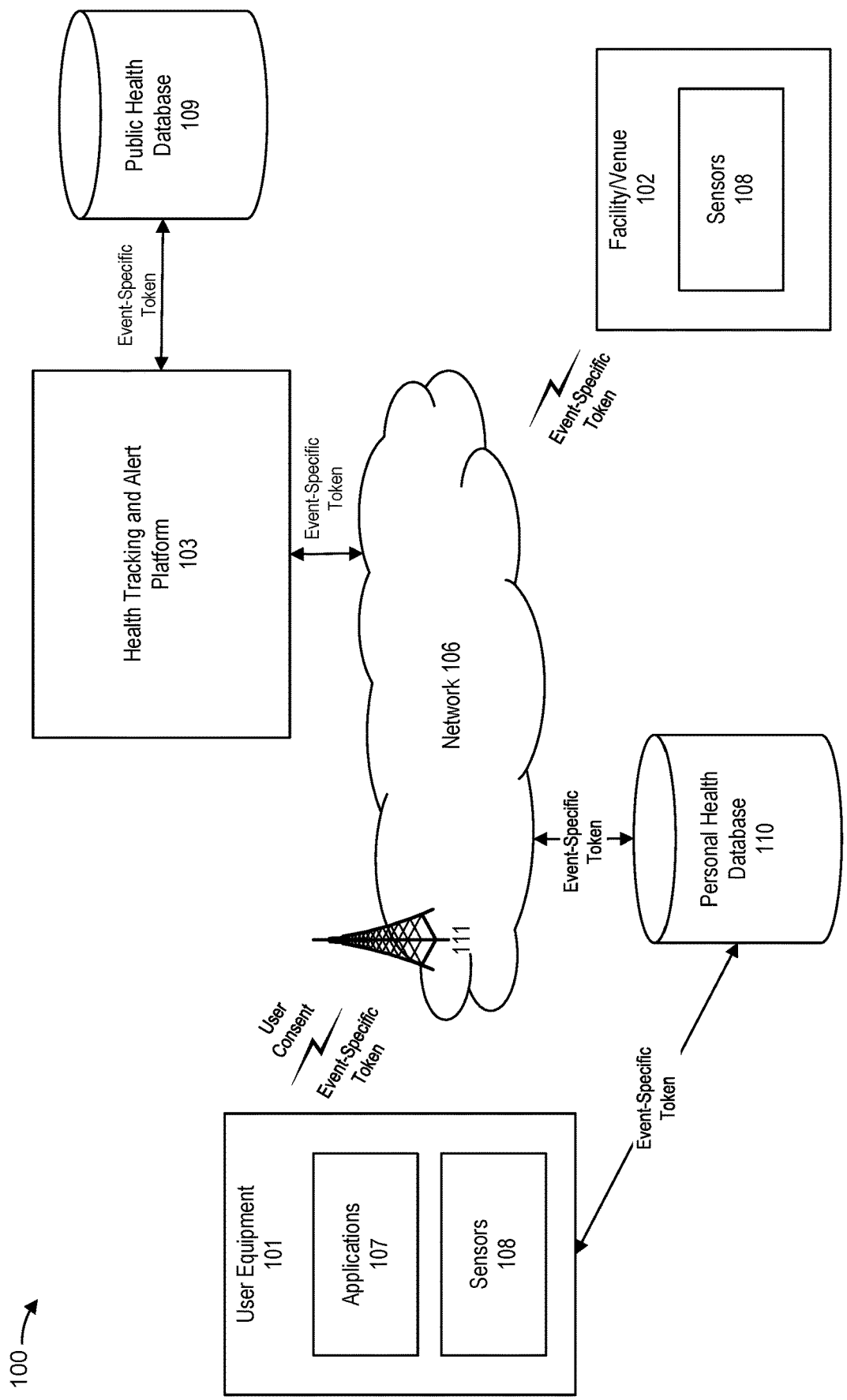
FIG. 1 illustrates a system of collecting, tracking and distributing health information.

The present disclosure will now be described with reference to the figures, which in general relate to technology for establishing a trusted relationship in a distributed system.

The spread of communicable disease poses a threat to humans and other organisms around the globe. In an effort to contain the spread of disease, many different systems and platforms have been developed. These systems, such as public health monitoring systems, often identify, analyze and trace data collected from a wide variety of sources.

Much of the collected data includes sensitive and personal data about individuals, often revealing names and other identifying information that would otherwise remain private. In order to maintain the privacy of information, particularly for data collected about individuals, the disclosed system employs a mechanism in which to generate event-specific tokens. The event-specific tokens may be generated by a facility or venue attended by the individual upon occurrence of some event, such as some anomalous activity. Once the event-specific tokens are generated, they may be distributed to individuals for storage with the collected data. The event-specific tokens may then be used to later identify and alert individuals that may be at-risk of being infected or carrying a communicable disease without revealing the identity of the individual.

It is understood that the present embodiments of the disclosure may be implemented in many different forms and that claim scope should not be construed as being limited to the embodiments set forth herein. Rather, these embodiments are provided so that this disclosure will be thorough and complete and will fully convey the inventive embodiment concepts to those skilled in the art. Indeed, the disclosure is intended to cover alternatives, modifications and equivalents of these embodiments, which are included within the scope and spirit of the disclosure as defined by the appended claims. Furthermore, in the following detailed description of the present embodiments of the disclosure, numerous specific details are set forth in order to provide a thorough understanding. However, it will be clear to those of ordinary skill in the art that the present embodiments of the disclosure may be practiced without such specific details.

Over the course of humanity, people have been exposed to disease. The spread of disease can affect individuals from local communities and regions to the entire globe. A disease that can spread from one individual (e.g., person, animal) to another via any one or more various forms of transmission (e.g., physical contact between the individuals, infectious microorganism) is said to be communicable. The spread of a communicable disease can lead to detrimental health effects (e.g., infection) and those who have had or continue to have interactions with the infected individuals. In some instances, the spread of disease occurs through close interactions between the infected individual and another individual. This is especially true in an enclosed environment such as an office space, school, public transit, etc. Within healthcare facilities such as a doctor's office and a hospital, the situation is aggravated by the infected individual visiting such facilities without knowing that he or she is infected. Due to close proximity with health workers (and the health workers engaging in further interactions with more patients), the disease may spread rapidly.

To slow or prevent the spread of disease, contact tracing and other forms of data management may be employed in which to obtain information on individuals (e.g., the date, the time, and risk factors with respect to the individual who may be infected—in the context of the present disclosure, this information is community interaction information) who are visiting a facility or venue which is vulnerable to the spread of disease. However, with the collection of personal information and data of individuals comes privacy and security concerns. For example, large amounts of data may be collected in which to determine whether an individual is at-risk of disease and infection. The sources of the data (e.g., sensors collecting the data) themselves may also be vulnerable to privacy and security issues given their often disparate and disconnected nature. These sources of data may include information provided to healthcare workers by individuals connected to an infected individual, social media information that is publicly available or shared by the information owner, or gathered from other systems (e.g., transportation systems or public health databases). To address privacy and security concerns in gathering this type of information, embodiments of the disclosed technology secure the privacy of collected information and data using separate databases (e.g., a database storing personal information and a database storing public information). In order to communicate and match the information and data stored in the two independent databases, event-specific tokens are generated and distributed to enable the flow of information, as described below.

FIG. 1 illustrates an example system for tracking and analyzing data. The system 100 includes, but is not limited to, user equipment (UE) 101, a facility or venue 102, a health tracking and alert platform 103, network 106, public health database 109 and personal health database 110. The system 100 collects, tracks and disseminates data (such as health information) using a variety of sensors places throughout the network. For example, personal sensors may be located in the UE 101 of each device or public sensors may be located in a particular public venue (such as a stadium) in which to measure a variety of conditions.

In one embodiment, UE 101 (or interchangeably referred to herein as a "personal monitoring device") can be used to collect personal health information (e.g., communicable disease information) from health care providers (via applications 107) and through sensors 108 in the UE 101. Collected data may then be used to monitor the health and wellbeing of the user (or individual), as well as to inform the public of any health-related issues. For example, the data is collected using the personal monitoring device 101 and can be transmitted to a disease tracking and alert platform 103 via network 106. The applications 107, as noted, may represent a health care provider application or serve as an interface to a health provider or other medical facility. Applications 107 may also be used to monitor and analyze collected data (or previously collected data—e.g., historical health data) from the sensors 108. For example, an application may monitor the heart rate or temperature of a user of the UE personal monitoring device 101, and may analyze the collected heart rate and temperature data to predict the health of the user. Sensors 108 may include any number of different sensors to collect data include, but not limited to, location information, health data (such as heart rate, temperature, oxygen levels, blood pressure, etc.), motion and tracking data, facial recognition software (e.g., to recognize a condition of the user, such as being tired or looking "ill"). Information collected by the user's personal monitoring device may then be sent to the health tracking and alert platform 103, as described further below. It is appreciated that the personal monitoring device 101 can be any type of mobile terminal, fixed terminal, or portable terminal including a mobile handset, station, unit, device, multimedia tablet, Internet node, communicator, desktop computer, netbook, laptop computer, Personal Digital Assistants (PDAs), or any combination thereof. It is also contemplated that the personal monitoring device 101 can support any type of interface to the user, such as wearable technology, including watches and glasses.

The health tracking and alert platform 103 (also referred to herein as "platform 103") collects and analyzes information relating to health threats and diseases, as well as distribute such information to organizations or entities for analysis and to people (or users) who may have attended (or encountered someone who has attended) an event at a particular venue in which a disease has been discovered or determined to have existed. In one embodiment, the platform 103 collects data using sensors remotely located in a public venue or facility, such as facility or venue 102. Non-limiting examples of public facilities or venues 102 include, theaters, shopping malls, buildings, parks, etc. Such sensors may also be referred to herein as public monitoring devices. Sensors 108 located in the facility or venue 102 collect information about people in attendance at the location. Sensors 108 located in the facility or venue 102 may also be referred to herein as "public sensors" or a "public monitoring device." In one embodiment, when a user enters a facility or venue 102, the sensors 108 may measure information about each of the users using the sensors 108 in the user's personal monitoring device 101 or via public sensors located throughout the venue. For example, public sensors (such as cameras) may measure crowds or clusters of individuals within a venue or track the movement of a particular user or number of users during an event at the facility or venue 102. Personalized sensors, such as sensors 108 within the personal monitoring device, may monitor a user's temperature or other health information during the event at the facility or venue 102. Sensors 108 in the public areas may also collect data regarding the location, movements and/or interactions of users and individuals inside or outside of the facility or venue 102 and can be continuously gathered using any detection means such as, but not limited to, cameras, RFID devices, an RFID detection grid, GPS devices, ultrasound devices, ultrasound detection grid, cameras, motion detectors, light beam detectors, image analysis systems and the like. For example, various sensors can be used to detect when individuals come within a specified physical proximity of one another and when an individual has performed sufficient hygiene procedures. Such collected data may be reported to the platform 103 in real time or any time after occurrence of an event at the facility or venue 102. Although termed "public" facility or venue, the facility or venue may also be privately owned, such as an office building or a hospital. In another embodiment, the platform 103 may acquire or collect data directly from the users. For example, the platform 103 may receive health data from a user's health care provider, either from the health care provider directly or from the user, e.g., via an application 107 (e.g., health care tracking application) on the users personal monitoring device.

When the collected data, such as communicable disease information, is received by the platform 103, the platform 103 can store the data in one or more secure repositories (e.g., a cloud computing environment), such as public health database 109. In one embodiment, the identity of people associated with the collected data is maintained securely and/or anonymously. In another embodiment, the anonymity of the collected data is maintained using event-specific tokens (explained below). In one embodiment, the platform 103 can associate a location of the data based on the location of the personal monitoring device 101 sending the information (e.g., using location tracking hardware or software) or based on a known location of a sensor 108 at the facility or venue 102 from which the data was collected. Each sensor 108 (e.g., personal monitoring device or public monitoring device) may include a unique identifier in which to associate the information with the collected data. Data collected from a personal monitoring device 101 may be user specific-data, whereas data collected from a public sensor (public monitoring device) may collect more generalized data (e.g., how many people enter a venue) that is not associated with a particular individual or user. In one embodiment, the public sensors may be associated with a facility (or venue) identifier and/or a location identifier within the facility or venue 102. The sensors 108 may also include an event-specific identifier. For example, if the sensor 108 is located within a stadium, the sensor 108 may be tagged with an identifier that identifies the specific event (e.g., a football game in one instance, and a concert in another instance). Events may also include an occurrence at a facility or venue 102, such as individuals encountering one another. For example, when an infected or potentially infected individual comes in to contact with other individuals at a facility or venue. Occurrence of an event may invoke generation of identifiers specific to the event or occurrence. These identifiers are referred to herein as "event-specific tokens." As discussed further below, event-specific tokens are generated and distributed within the system 100 in order to match information and data with the occurrence of events, while preserving the privacy of the information and data. These event-specific token, based for example on facility/venue ID, date and time, proximity of contact, etc.) may also be used to provide public health notifications and alters to individuals based on the specific event, as opposed to using a user ID or user token.

Once enough data has been collected, the platform 103 can prepare the collected data for analysis by the platform 103 (explained below). The collected data may include the data collected from public monitoring devices that is stored in the public health database 109. The collected data may also include the data collected from personal monitoring devices that is stored in another secure repository, such as the personal health database 110. The personal health database 110 maintains user's personal health data and information in a secure manner. Data stored in the personal health database 110 remains private. Information collected from a personal monitoring device 101 may be transferred (e.g., uploaded or downloaded) directly from the personal monitoring device 101 to the personal health database 110, or network 106. In one embodiment, data stored in the personal health database 110 is accessible only to individual users and may not be accessed by the platform 103 or facility (or venue) 102 without the express permission or consent of a user. In one embodiment, data collected from the personal monitoring device may be analyzed by the platform 103 only after appropriate permission or consent is obtained by a user In one embodiment, the user personal information stored in the personal health database 110 may be anonymized by use of an event-specific token. That is, the event-specific token may anonymize the user personal information using IDs or pseudo IDs that are associated with a specific-event occurrence. Event-specific token generation and distribution is described below in more detail. In another embodiment, the analysis can be performed in conjunction or independently with another system such as the Center for Disease Control and Prevention (CDC), World Health Organization (WHO), etc. (not shown). The analysis may also be specific to one or more events that occurred at the facility or venue 102, to a specific time frame at the facility or venue 102 (e.g., a specific day or hour), etc.

Once the collected data has been analyzed, the platform 103 can then notify or alert people about any detected issues. For example, analysis of the collected data may result in detection of an anomaly, such as an outbreak, pandemic, epidemic or bioterrorism act. Such an anomaly may be detected using, for example, a detection algorithm that searches for keywords, relationships between location of a data source and the time and date of the reported source, whether reported events involve a human, group of humans, etc. Detection of such an anomaly may, for example, trigger an automated public heath alert and/or provide a cohesive picture of the threat and orchestrate a coordinated response. In one embodiment, the alert information can be selectively provided based on the location of the user's personal monitoring device such that only affected users are notified of the potential health threat. The location of the personal monitoring device can be provided by the personal monitoring device itself, or determined by the network. In some scenarios, the message is sent via a text messaging service or an electronic mail service. In other scenarios, the platform 103 can send the analysis and/or alert information via a web service.

As illustrated, the system 100 comprises the personal monitoring device 101 and facility/venue 102 having connectivity to the disease tracking and alert platform 103 (and public health database 109) and the personal health database 110 via a network 106. The network 106 may include, but is not limited to, a data network, a wireless network, a telephony network, a messaging network, or any combination thereof. It is contemplated that the data network may be any local area network (LAN), metropolitan area network (MAN), wide area network (WAN), a public data network (e.g., the Internet), or any other suitable packet-switched network, such as a commercially owned, proprietary packet-switched network, e.g., a proprietary cable or fiber-optic network. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, code division multiple access (CDMA), wideband code division multiple access (WCDMA), wireless fidelity (WiFi), satellite, mobile ad-hoc network (MANET), and the like.

In one example embodiment, the platform 103 can send messages (e.g., alerts and notifications) to users at their personal monitoring devices 101. In another example embodiment, the platform 103 can send a group of users messages to their respective personal monitoring devices. The platform 103 can send messages to a single user or a group of users based on geographic location, age, movement history, proximity of users to one another during a specified time period, or any other number of different factors. Messages may include any format, such as text, SMS, email delivery, push notifications to an application on the personal monitoring device, etc. in which to notify and alert users of any health threats or diseases tracked by the platform 103.

Figure 2:
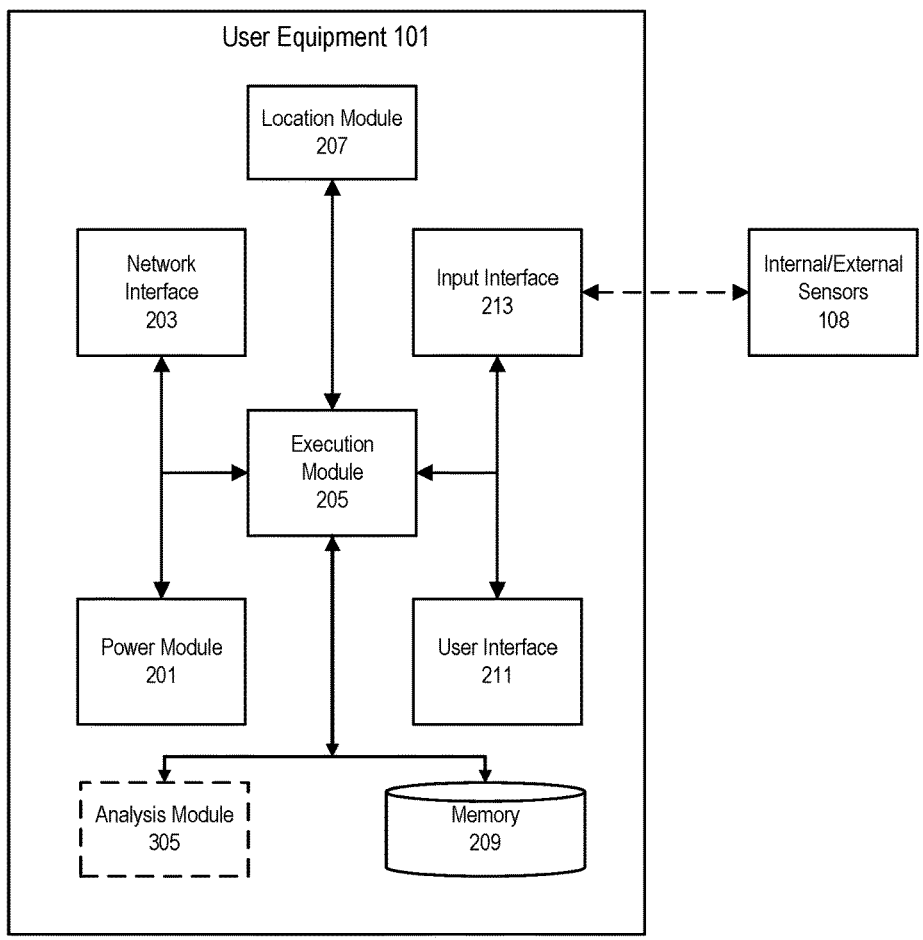
FIG. 2 illustrates an example embodiment of a personal monitoring device and a platform for collecting and analyzing data in the system of FIG. 1.

FIG. 2 illustrates an example embodiment of a personal monitoring device and a platform for collecting and analyzing data in the system of FIG. 1. The personal monitoring device 101 includes one or more components for providing collection of data (e.g., health data) and presentation of alerts and notifications related to the collection of the data (both from the data collected using the personal monitoring device and using public monitoring devices). As illustrated, the personal monitoring device 101 includes a power module 201, a network interface 203, an execution module 205, a location module 207, a memory 209, a user interface 211, an input interface 213, sensors 108 (internally or externally) and an optional analysis module 305. The analysis module 305 is described below with reference to FIG. 3.

The power module 201 provides power to the personal monitoring device 101. The power module 201 can include any type of power source (e.g., battery, plug-in, etc.). Additionally, the power module 201 can provide power to the components of the personal monitoring device 101 including processors (not shown), memory 209, transceivers (not shown), or the like.

The user interface 211 can include various methods of communication. For example, the user interface 211 can have outputs including a visual component (e.g., a screen), an audio component, a physical component (e.g., vibrations), etc. User inputs can include a touch-screen interface, a scroll-and-click interface, a button interface, a microphone, etc. In one embodiment, the visual or audio component of the user interface 211 can prompt a user to retrieve or input information regarding health and disease information. For example, the user can be prompted to enter data about a recent health issue (e.g., becoming infected with a disease). In another example, the visual component can display an analysis (e.g., an alert or notification) performed by the personal monitoring device 101 or an external system, such as platform 103. The analysis may be presented in the form of visual or audio, such as sound, text, graphs, diagrams, or as other common forms of interfaces (e.g., an email interface or an SMS interface). In the event of a disease outbreak at the facility or venue 102 the system 100 may deliver alerts or warnings to by automatically selecting a specific group of users or target audience who may be at high risk of entering the venue (or whom have previously entered the venue), and broadcast emergency warnings to them via the personal monitoring device 101.

In another embodiment, the personal monitoring device 101 includes an input interface 213. The input interface 213 can include manual user inputs such as a touch-screen interface, a scroll-and-click interface, a button interface, etc. as well as other (e.g., automated) input mechanisms. The personal monitoring device 101 can receive input from a processor and/or sensor. In one embodiment, the input interface 213 of the personal monitoring device 101 interfaces with internal/external sensors 108. Internal sensors may include, but are not limited to, image sensors (e.g., camera), microphone, motion sensors (e.g., accelerometer, gyroscope, proximity sensor), light sensors, global positioning system (GPS), etc. For example, the personal monitoring device 101 includes a location module 207. The location module 207 can determine a user's location using, for example, a triangulation system such as a global positioning system (GPS), A-GPS, Cell of Origin, or other location extrapolation technologies. The location module 207 may also utilize multiple technologies to detect the location of the personal monitoring device 101. In one embodiment, GPS coordinates and/or a cell-ID are embedded into messages sent to the platform 103 to notify platform 103 of the current location of the personal monitoring device 101. In another example, a sensor of the personal monitoring device 101 may take a user's temperature or measure their blood oxygen levels. Applications 107 residing on the UE 101 may act as an interface with the sensors to receive input and analyze collected samples. In another embodiment, the GPS coordinates and/or cell-ID are retrieved by the platform 103 to determine a historical location of the user in which to track previous movements for matching against health and disease information.

The personal monitoring device 101 may also communicate with external sensors 108. External sensors 108 may also be any of the same as the internal sensors, and include any other type of health monitoring apparatus that is compatible with the 101, such as but not limited to blood pressure machines, cognitive function sensors, ear nose and throat (ENT) monitoring devices, pulmonary health monitoring devices, etc. For example, a digital image can be captured using a sensor (e.g., camera) of a blood sample, and the processor may determine whether the blood sample is positive for a disease or infection. Other types of external sensors 108 may include routers, access points or base stations, which collect information and data about individuals and or devices owned by the individual. For example, a base state may be able to determine the path or location of a user based on location information stored in the base station as a mobile device moves from base station to base station, or a router in a vehicle may be able to provide the location of the vehicle during a period of time. In one embodiment, data collected from the internal/external sensors 108 may be stored, for example, in memory 209.

The execution module 205 can initiate transmission of the collected data (e.g., health and disease information) to the platform 103 or the personal health database 110 via the network 106. Transmission of the health and disease information may be transmitted manually or triggered automatically based on a conditions or rules (e.g., transmit health and disease information to the platform 103 when a user has a temperature above 99.9 for 3 days in a row) set in the personal monitoring device 101 (e.g., set in an application). In one embodiment, the network interface 203 is accessed by the execution module 205 to communicate with the platform 103 (and public health database 109) and personal health database 110 via various components, such as transmitters, receivers, transceivers, etc. (not shown). In another embodiments, the platform 103 can prompt the execution module 205 to collect data about health and disease information. The execution module 205 can collect the health and disease information via the user interface 211 and input interface 213 and transmit the health and disease information to the platform 103 via the network interface 203. In other embodiments, the platform 103 can provide health and disease analysis information for the personal monitoring device 101. The execution module 205 can receive the analysis and present the analysis via the user interface 211.

Figure 3:
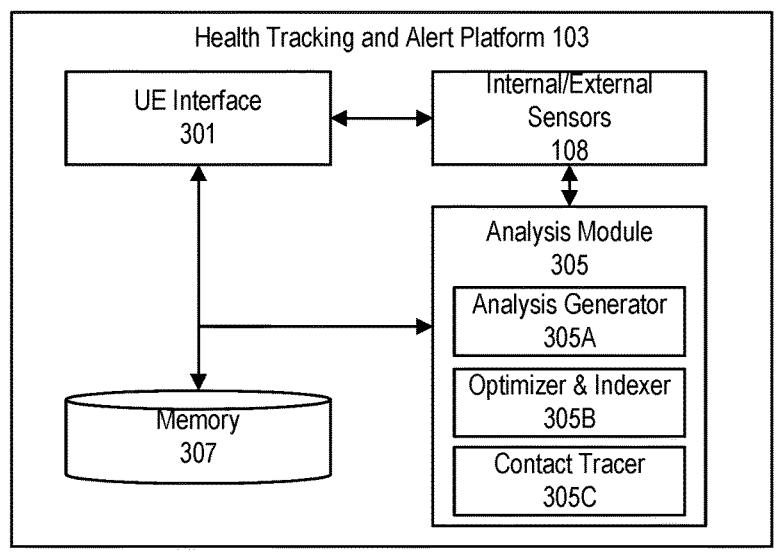
FIG. 3 illustrates an example embodiment of the disease tracking and alert platform of FIG. 1.

FIG. 3 illustrates an example embodiment of the disease tracking and alert platform of FIG. 1. The disease tracking and alert platform 103 (platform 103) includes components for collecting, tracking, analyzing, and disseminating health information. In particular, the platform 103 includes a UE interface 301, internal/external sensors 108, an analysis module 305, and a memory 307. The platform 103 also communicates with the public health database 109 and personal health database 110, for example via network 106.

The UE interface 301 can be utilized to communicate to a personal monitoring device 101 of a user either directly or via platforms and systems. In some examples, the UE interface 301 utilizes electronic components such as transceivers and processors to transmit and receive data to the personal monitoring device 101. In one embodiment, the UE interface 301 includes initiating transmission (e.g., via messaging infrastructure) of and receiving electronic messaging (e.g., SMS messaging, e-mail, instant messaging, etc.) to the personal monitoring device 101. In another example, the UE interface 301 includes an interactive web component. The interactive web component can work in conjunction with applications 107 of the personal monitoring device 101 or via a web interface. In this example, users can update information (e.g., update disease information used for analysis) conveyed by the UE interface 301 of the platform 103. Such information may also be provided to other personal monitoring devices 101 in order to provide them with updated information about a particular facility/venue or event (e.g., a user interested in disease spread in an athletic stadium). Additionally, the UE interface 301 can be utilized to send disease information and analysis to research agencies and firms interested in the data.

The analysis module 305 includes analysis generator 305A, optimizer and indexer 305B and contact tracer 305C. The analysis module 305 collects information from internal/external sensors 108 in the form of data which is able to get processed in order to track interactions and assess risks of potentially infected individuals. In one embodiment, the analysis module 305 communicates with the public health database 109 and personal health databases 110 to retrieve and analyze collected data. The analysis module 305 can also receive data directly from a personal monitoring device 101 via the UE interface 301. The analysis module 305 can store the data (e.g., infection and disease information) retrieved from the databases in a memory 307 and process the information using one or more processors (not shown). In some embodiments, infection and disease information includes health, location, timing and other disease-related information (e.g., a disease name, a disease strain, etc.) about one or more people having a communicable disease or infection. In some embodiments, and in order to protect the privacy of users and the sensitivity of data, activities and location data are anonymized, consented to and aggregated before analysis by the analysis module 305. In one embodiment, the aggregation of data can be based on conditions or thresholds set by the platform 103 such that unrelated people, events and information are filtered out. In other embodiments, the information is tagged with or includes an event-specific token. The even-specific token may be distributed between the platform 103 and the user's personal monitoring devices and the facility/venue in order to avoid sharing of sensitive data, as well as to link users or groups of users (discussed further below). In one example, the analysis module 305 can retrieve infection and disease information from a personal monitoring device 101 and determine that the personal monitoring device 101 is assigned to a certain geographic location. In one embodiment, the analysis module 305 can determine whether a user has had any contact with other infected users via contact tracing. For example, the user may report having contact with an infected individual, or the platform 103 upon analysis of information may determine that certain infected users have come into contact with one another based, for example, on proximity detection sensors within individual personal monitoring devices. In another example, the analysis module 305 may query the number of potentially infected users with a specified type of virus or virus source. Any number of different mechanisms may be employed to report contact with infected individuals.

In one other embodiment, the analysis module 305 may assess the likelihood that a user is sick by evaluating physiological characteristics. For example, if user has a higher than normal temperature, increased pulse, increased heart rate, disturbed sleep pattern and low physical activity level, the analysis module 305 may infer or predict that a user is ill or falling ill. The analysis module 305 may use this information to predict the spreading of infection and disease to other users and individuals based on the proximity of the infected user to other users. In one embodiment, the analysis module 305 inputs the values of the physiological characteristics (e.g., numerical values for body temperature, pulse rate, heart rate, etc.) into a probabilistic model or algorithm to determine a likelihood that user is sick. The probabilistic model may be built using previously collected physiological data.

The physiological information may be coupled or combined with non-physiological information such as location of user, time of day, and calendar or schedule of the user to determine the likelihood that user is sick with a communicable disease. In one implementation, the analysis module 305 accesses the user location and calendar to determine whether the user is sick with a communicable disease. For example, the analysis module 305 may learn that user is at home when he or she is scheduled to be in the office at a meeting. The non-physiological information can increase or decrease the likelihood that user is sick. For example, in the above case, the fact that user is at home rather than in the office increases the likelihood that user is sick. In one embodiment, the non-physiological information may also be input into the algorithm to update and revise the likelihood that a user is sick.

Additionally, information may be input into the analysis module 305. For example, in one embodiment, the analysis module 305 includes an algorithm to construct contact tracing output based on certain input parameters (e.g., individuals diagnosed with an infection). Using the algorithm, the analysis module 305 may determine other individuals who have had contact with the individuals diagnosed with the infection. Based on parameters such as the proximity of contact, the method of contact, etc., the algorithm of the analysis module 305 builds a list of potentially infected persons. If prior information is available on certain individuals, the algorithm is able to learn from the prior information to build a more accurate model which is able to better form and assess risk profiles. For example, the analysis module 305 may receive pre-entered information or receive information on an individual pertaining to past events. Based on all of the provided information, the analysis module 305 may trace the individuals who might have been exposed to an anomalous event and notify the individuals using, for example, the analysis generator 305A.

After analysis module 305 processes the interaction data, the processed data is mapped and stored within a repository. For example, the analysis module 305 can store the infection and disease information with information including the assigned geographic location, timing information about when the disease information was taken, and information about the disease involved and the health (e.g., deceased, contagious, the state of the symptoms, etc.) of people associated with the disease. The analysis module 305 can then retrieve information from the public and personal (when granted permission) health databases 109 and 110 and process the information to determine trends and other analysis of the spread of infection and disease using one or more geographic locations. In one embodiment, the information is tagged with an event-specific token in which to secure and privatize the data. Access to the information may only be granted when event-specific tokens are matched and validated by the system, as explained below.

The analysis generator 305A may generate alerts to notify users of the potential risk of infection based on the analyzed information by the analysis module 305. The analysis module 305 may then notify users by sending alerts, via the UE interface 301, to a personal monitoring device 101 configured to receive (e.g., via an application 107 or a web interface) the information. For example, when it is determined that the user is sick, the analysis generator 305A may provide the user with a course of action to prevent the further spread of the communicable disease. The analysis generator 305A can suggest that user stay home, stay away from certain areas (nursing homes, hospitals, etc.), and/or schedule an appointment to see his or her doctor. In some embodiments, analysis generator 305A also notifies user doctor to let the doctor know that user is sick so that the doctor can check up on user. The one or more courses of action generally include a strategy to control the spread of the communicable disease. The strategy to control the spread of the disease can include one or more of household quarantine, individual quarantine, geographic quarantine, social distancing, hospitalization, school closure, work place closure, travel restrictions, public transit closure, therapeutic treatment or intervention, prophylactic treatment or intervention, vaccination, provision of protective clothing, provision of masks, warning or notification of others, and additional point-of-care testing.

Conditions that are not communicable, such as a headache, may result in different actions performed by the analysis module 305. For example, the analysis generator 305A would not warn the user to stay away from others and public places, or warn others who were exposed to user. However, the analysis generator 305A may still provide suggestions or recommendations to user, such as seeing a doctor or getting rest. In some embodiments, analysis module 305 may attempt to identify the non-communicable disease by matching the symptoms and signs exhibited by user with known non-communicable diseases. In other embodiments, the physiological information of users may be periodically monitored to determine how long a user is sick or remains contagious. Once the risk level of infection goes down, the analysis generator 305A can notify the user that he or she is allowed to resume normal activities, such as going outside or resuming work at the office.

The optimizer and indexer 305B optimizes and indexes information obtained from the sensors 108 and stored in the public health database 109 and personal health database 110. In one embodiment, the data is optimized by grouping data by the time and space where a particular user (e.g., a person who may be identified as someone infected during an event) has been found. This grouped data may then be indexed using the unique identifier for the user, such as the identifier (ID) of a personal monitoring device. In one embodiment, the ID is part of the event-specific token. In one embodiment, the ID can be used to further identify the user by social security number, passport number, and biometric data such as a fingerprint or a facial feature. Such information may also assist in linking the user (and ID) to health and medical information about a user, such as through a doctor's office or hospital that has records of the user.

The contact tracer 305C can perform contact tracing. Contact tracing is the identification and diagnosis of persons of who have come in contact with an infected person. If it is known that the infected individual has engaged in extensive interactions with others or the infected individual has travelled over a long distance to another discrete location (city, state, country, etc.) via ground, air or sea transportation, then further analysis will potentially be needed to trace the contacts within multiple locations. In one embodiment, the contact tracer 305C accounts for the interactions of individuals to determine the risk of a potential individual obtaining an infection during an event.

FIG. 4 illustrates an example flow diagram for collecting and analyzing data for contact tracing. In embodiments, the flow diagram may be computer-implemented methods performed, at least partly, by hardware and/or software components illustrated in the various figures and as described herein. In one embodiment, the disclosed process may be performed by the system and components in FIGS. 1, 2 and 6. In one embodiment, software components executed by one or more processors, such as processing unit 914, performs at least a portion of the process. For purposes of the example that follows, an analysis module (in the platform or the personal monitoring device) implements the process.

At step 402, the analysis module 305 receives data collected from the internal/external sensors 108. As noted above, the sensors 108 may be located within a personal monitoring device 101 of the user or at a facility or venue 102 open to the public. The data collected from the sensors 108 is processed by the analysis module 305. The collected data is analyzed for information relevant to users that are potentially at-risk of exposure to an infection or disease at an event. The event may have occurred, for example, at a particular facility or venue during a particular time frame. The information may include or be filtered for a user's medical history, travel history, and the like. For example, for purposes of example, assume the spread of a disease in the state of Florida. The disease may have been spread due to the exposure to of handling chickens in a slaughterhouse. Investigators may be set forth to examine the number of people potentially exposed to the chickens, as well as examine any outbreaks that may have affected individuals at the community, regional and state level. To assist in the investigative process, the analysis module 305 may examine the travel history of the individuals infected with the disease. After examining the travel history, the analysis module 305 may determine that the individual infected with the disease has taken a business trip to another slaughterhouse in the state of Iowa, in which chickens at that business venue are prone to infection of the disease. In this scenario, the travel history is included (or filtered to include) in the user data as relevant information with respect to the individual of interest. The information that is collected may then be stored for later retrieval. The stored data will also include or be tagged with an event-specific token generated at step 404. The event-specific token, when used in conjunction with stored data, can be used to maintain the privacy of data.

At step 404, event-specific tokens are generated upon occurrence of an event, such as individuals or users visiting a venue or facility near or at the same time. The event-specific tokens may be exchanged between parties (e.g., user and facility or venue) of the system 100. For example, when users attend an event hosted by a facility or venue 102—either during the event or subsequent to attendance at the event, the event-specific tokens are generated by the facility or venue 102 (or by an independent third party, such as the platform 103). The event-specific tokens, as described further below, will identify the users in attendance at the event as well as the facility or venue being visited. Notably, the event-specific tokens are tied to the occurrence of an event (the specific event being attended), as opposed to a user ID or a user token.

As users attend the facility or venue 102, personal data generated by the personal monitoring device and accompanying sensors are uploaded to the personal health database 110 (either during the event or later). The personal data stored in the personal monitoring device 101 or personal health database 110 is also tagged with the event-specific token related to the event. The personal data may later be retrieved from the personal health database 110 by the user. In one embodiment, the event-specific token secures and protects the identity of the user and any user information stored in the database. In one embodiment, the personal data for an individual user is uploaded to the personal health database 110 into a portion or partition of the personal health database 110 that is separate and private from other individual user data and information. The portion or partitions of data may also be referred to herein as "private droplets."

In one embodiment, the event-specific tokens include information about the venue or facility ID (or the public monitoring device ID), the personal device ID, date and time, number of users, measurement data, etc. More specifically, FIG. 5A illustrates an event-specific token 500A for storage in the public health database 109 that tags the data collected from public monitoring devices (e.g., public sensors). The event-specific token includes, for example, the venue or facility ID, the device ID (personal monitoring device), the date/time of the event, the event ID, the number of users, sensor measurements, signatures of users and the venue or facility device key.

FIG. 5B illustrates an event-specific token 500B for storage in the personal health database 110 that tags the data collected form personal monitoring devices (e.g., personal sensors). The event-specific token includes, for example, the venue or facility ID, the device ID (personal monitoring device), the date/time of the event, the event ID, the number of users, sensor measurements, signatures of the venue or facility and the user device key. In one embodiment, the user device key is different for each event. It is appreciated that the format and fields of the event-specific token may vary to include fewer or additional fields of information, and that the depicted embodiments are non-limiting examples.

In the event-specific tokens 500A and 500B depicted in FIGS. 5A and 5B, the facility ID identifies a facility or venue that a user visits during an event. For example, a user may visit a shopping mall. The shopping mall may be identified using a facility ID, such as a name, number, address or the like. Similarly, the device ID identifies a user device, such as the personal monitoring device (e.g., a mobile phone with sensors). In one embodiment, the device ID may be the name of the personal monitoring device, the serial number of the personal monitoring device or any other identifying information, while maintaining the privacy of the user. In one embodiment, the facility ID or device ID may be a pseudo ID (e.g., a user name or facility name that does not identify the facility or user by name but is otherwise associated with the facility or user). In one embodiment, the pseudo ID may be generated by a pseudorandom number generator that outputs a sequence of outwardly random numbers.

A date and time stamp field may also be included in the event-specific token and represent that date and time a user attended a facility or venue in which an event occurred. The event-specific token may also identify the number of users in attendance at the event and facility during the same date and time (or during a specified time period), as well as include measurements made by sensors. In the embodiment of FIG. 5A, the sensor measurements represent measurements made by the public monitoring device (e.g., sensors placed throughout a facility or venue). In the embodiment of FIG. 5B, the sensor measurements represent measurements made by the personal monitoring device (e.g., sensors in a mobile phone or wearable device).

The event-specific tokens may also use a key exchange technology. For example, a two-key system may be employed in which public and private keys are used to encrypt messages with one key and decrypt the message with another. Any number of different key exchange technologies may be employed and is outside the scope of this document. During generation and distribution of the event-specific token, the facility (or venue) and users in attendance at the facility exchange public keys (e.g., signatures) of the two-key system. The facility device key (e.g., the facility private key) is used to verify the event-specific token 500B of a user is valid during communication. The event-specific token 500A stored in the facility includes the signatures from the users in attendance of the event and the keys for generating the facility signature (e.g., the public key). The user signature corresponds to the user keys (e.g., private keys, which may be updated or changed to avoid tracing of the user) in the event-specific token 500B. In one embodiment, the user keys are only stored in the event-specific token 500B of the personal health database 110 (or private droplets in the database). More specifically, the event-specific token 500A includes a copy of the user's signatures, which may be verified by the platform 103 matching the user's signature in the event-specific token 500B to the user signature in the event-specific token 500A. The event-specific token 500B distributed to the individual user includes the signature from the facility (or venue). The signature of the facility is used to verify that notifications, including the event-specific token, sent by the facility are valid. For example, a user may notify the platform 103 that she has been diagnosed with a positive infection within one week of attending a specific event. When the user communicates with the platform 103, the communication includes the event-specific token 500B previously distributed to the user by the facility. The event-specific token 500B may then be used by the platform 103 to verify that the user is valid (e.g., that the user attended the specific-event) by conferring with the facility that stored the user signatures in the even-specific token 500A.

At step 406, the analysis module 305 determines whether to process the collected data as private or public. In general, data that is collected or captured from the user's personal monitoring device is considered private data, whereas data collected or captured from sensors using public monitoring devices (e.g., located in public environments) are considered public data. Examples of private data typically include personal data, such as name, bank information, personal health and health history data, device information (e.g., device ID), etc. Examples of public data typically includes information that is collected in public, such as neighborhood health information, visiting patterns and anomalous behavior data.

At step 408, personal (or private) data is stored in personal storage, such as personal health database 110 at step 410. Public data is stored separately in public storage, such as public health database 109. In one embodiment, the public data collected from sensors is aggregated for statistical analysis. In one further embodiment, the aggregated data is grouped or clustered according to categories. Categories may include, but are not limited to, time, venue, event, movement pattern, illness, etc. For example, the aggregated data may be clustered according to users that have fallen ill with a disease during a specified time period. In another example, the aggregated data may be clustered according to a specific event attended by users or a venue in which the users visited. Additionally, any user identifying information is removed from the aggregated and/or clustered data prior to analysis so as to privatize the data and make it anonymous to other users or individuals. In one embodiment, the privatized data is tagged with an event-specific token in which to anonymously identify users and individuals. That is, the event-specific token identifies users by specific-events instead of user information, such as user ID or user tokens.

At step 412, the analysis module 305 statistically analyzes the collected data. For example, the clustered data may be transformed into organized (e.g., by optimizer and indexer 305B) data pertaining to individuals who may be at-risk of infection or spreading disease. In one embodiment, individuals identified as at-risk of infection or spreading disease may be identified using the event-specific token. In some embodiments, the organized data is optimized, indexed, and analyzed by analytics module 305. During optimization and indexing, the optimizer and indexer 305B may examine individual users or groups of users by category and index those individual users or groups of users using an event-specific token. This data may be used by the contact tracer 305C to determine the interactions of individuals and groups of individuals, including travel history, movement or visiting patterns, neighborhood health information, and other factors relevant to contact tracing. Over the course of time, the data collected by the sensors may be updated based on newly received sensor information, which in turn allows the analysis module 305 to update information about individual users and groups of users, also discussed below with reference to FIG. 6. Likewise, the public health database 109 and personal health database 110 may be updated to reflect any changes. For example, a user may be originally diagnosed with an infection based on a visit to a medical facility. This information may originally have alerted the platform 103 to notify other users and individuals that were in contact with the infected user. Subsequently, the user may be cleared by the medical facility as no longer being infected. This may prompt the system to discontinue any notifications or alters to other users and individuals that may subsequently come into contact with the formerly infected user.

The organized data can be assessed and permits the comparison of the data associated with one individual with the data associated with another individual or group of individuals. In embodiments, comparisons are made between an unidentified individual who is potentially infected and another individual or group of individuals who may be infected using biometric data comparison. Data associated with geographic distribution, clinical risk factors, demographics or other sources of exposure, such as social networks may also be evaluated. All of this data can be complied, aggregated and analyzed by the analysis module 305 in order to facilitate the integration, synthesis, and visualization of resultant information pertaining to the control, surveillance, and prevention of spreading of the infection or disease. A final assessment of the data may provide a profile of individuals at-risk for contracting an infection and spreading disease during an event at the community, regional, state and country level. In one embodiment, the level of risk for infection or spreading disease may also include a designation as to the severity of the risk, such as the risk of infection being "high," "medium," or "low," or the risk may be "scored" accordingly to some pre-defined scale.

At step 414, the analysis module 305 determines if an at-risk person (or group of people) is found. The analysis done by analysis module 305 in step 412 yields an assessment of potential individuals at-risk of contracting a disease or an infection during an event and potential individuals who have contracted an infection or potentially spread disease during an event. If the analysis module 305 determines that an at-risk individual is found, then the analysis module 305 identifies at-risk individuals at step 418 and prepares a list of the at-risk individuals. In one embodiment, and to preserve the privacy and information of individuals, the names and personal information of the at-risk individuals are securely stored and hidden from view or washed from the data entirely. For example, individuals may be "identified" using an anonymous identifier that corresponds to an event-specific token generated and distributed for the specific event attended by the individual. The at-risk individual list and associated information may also be kept secure (i.e., confidential) among the users who are working to mitigate the spread of the disease and infection by employing (but not limited to) user account controls and various encryption techniques which may be incorporated into the analytics module 305. At-risk individuals may be notified at step 420 using the analysis generator 305A, described above.

If analysis module 305 determines that a risk is not found at step 414, then further analysis and tracing may be terminated at step 416.

Figure 6:
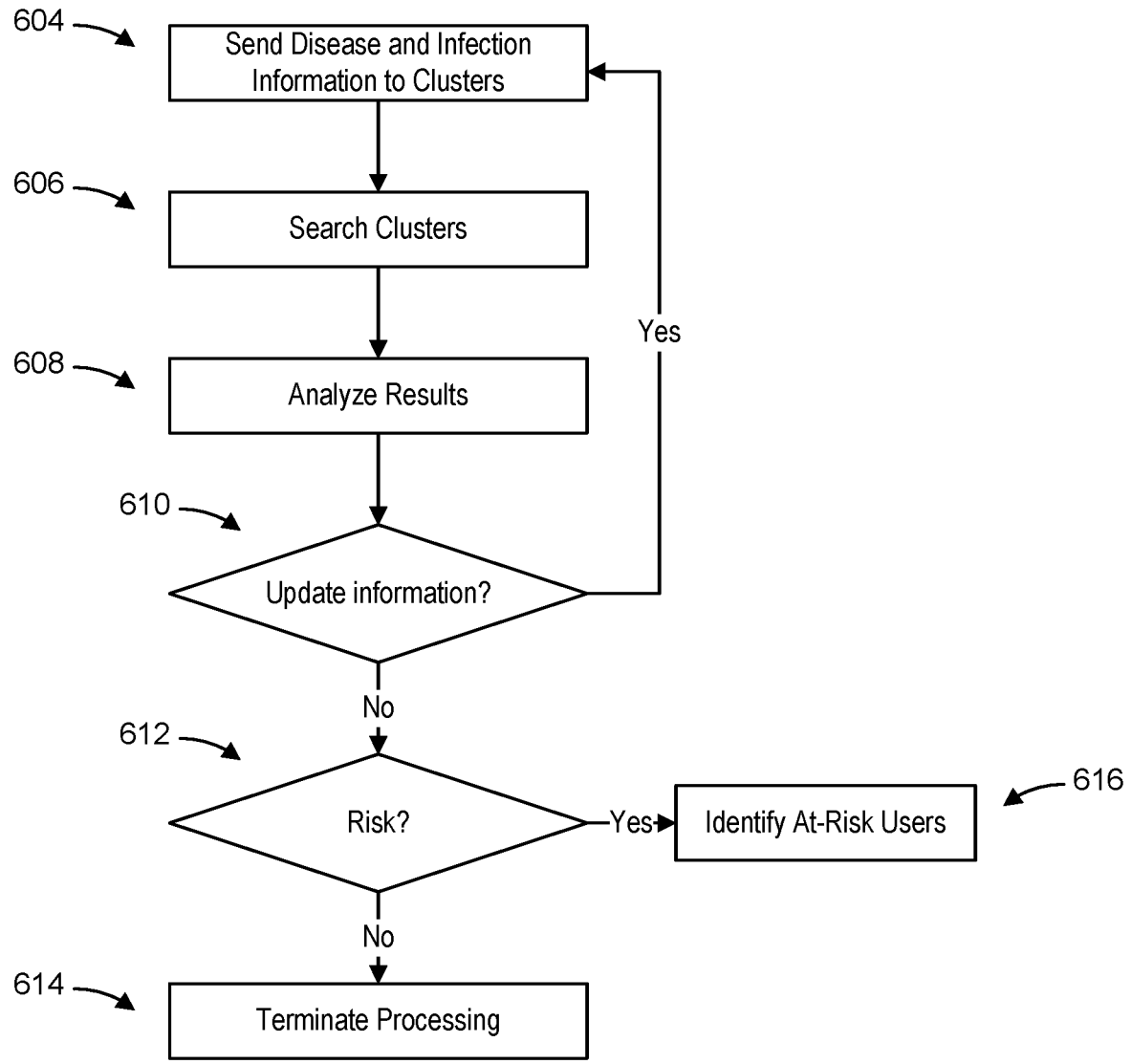
FIG. 6 illustrates an example flowchart of identifying at-risk users.

FIG. 6 illustrates an example flowchart of identifying at-risk users. In embodiments, the flow diagram may be computer-implemented methods performed, at least partly, by hardware and/or software components illustrated in the various figures and as described herein. In one embodiment, the disclosed process may be performed by the system and components in FIGS. 1, 2 and 6. In one embodiment, software components executed by one or more processors, such as processing unit 914, performs at least a portion of the process. For purposes of the example that follows, an analysis module (in the platform or the personal monitoring device) implements the process.

The analysis module 305 receives collected data regarding users attending an event at a facility. The collected data can be any number of different sensor measurements, such as body temperature, medical history, travel information, passport information, salient health features (e.g., cuts or bruises), or the like. As discussed above, the collected data may be used by the analysis module 305 to assess the risk profile of users. As disease and infection is contagious, one embodiment analyzes the collected data to map a spread of the disease or infection contracted by users. Mapping may be based on any number of different factors, such as the level of contagiousness, susceptibility of an individual user, diffusion of the disease, amount of time in contact with an infected individual, etc.

At step 604, the information may be grouped or clustered into categories by the analysis module 305, as noted above. In one further embodiment, clusters may also be categorized based on location (e.g., where an infected user has traveled). For example, if it is known that an infected individual has had extensive interactions with others, or if the individual has travelled over a long distance to another location (city, state, country, etc.) via ground, air or sea transportation, then analysis is carried out in order to trace the contacts in the multiple locations. This further analysis helps to provide a more extensive contact tracing.

In step 606, analysis module 305 searches the clusters of information. The information can be compiled into a hierarchical level of clusters. The levels may be created based on a logical level such as public transportation (e.g., a bus) within city limits, which analyzes the data based on location clusters (e.g., where the bus has traveled within the city). This may be in addition to any analysis of other individuals that may have been on the bus with an infected user. The location cluster within the state may also be used to evaluate other clusters of data. For example, at a state level (as opposed to city level), each cluster of data at the city level may be aggregated into groups or clusters for further analysis. The analysis in on embodiment may be performed by contact tracer 305C. The contact tracer 305C may analyze the various levels of clusters and extract information in order to obtain information on the contact information (e.g., using event-specific tokens) of the people who are at-risk and to provide actionable items which can be fed back to the various clusters as needed. For example, and for purposes of discussion, it has been determined that the infected individual has travelled via bus from country A to country C through country B. The individual has close contact with another person who continued his journey to country D. These interactions and the potential risk will then be analyzed by the contact tracer 305C. The countries A, B, C, and D are treated as clusters and the countries of A, B, C, and D will be properly notified by the analysis generator 305A of analysis module 305.

At step 608, the analysis module 305 analyzes the results (which, in the example above, are derived from searching through the clusters in step 606 and the collected data, including infected individual information). If a match for an at-risk candidate is found, analytics module 305 returns information on the potentially infected candidate. In some embodiments, clusters may be identified that will influence the determination of whether a potentially infected candidate will be found. For example, if the infected individual has provided or identified locations she has visited, then these clusters should be further analyzed and optimized. In instances where the clusters have been determined to have no effect on identifying an infected individual (e.g., the individual has stated that a specific location has not be visited), the clusters may be removed from the analysis and optimization. Thus, the analysis module 305 may perform optimization and filtering out the "irrelevant" clusters and focus on the established clusters.

At step 610, analysis module 305 determines if there is any updated individual information. For example, new data may be collected by sensors 108 after completing the analysis in step 608. If additional data has been collected, the new collected data from the sensors 108 may lead to a different assessment after performing the analysis in step 610. Thus, if at step 610, the analysis module 305 determines there is updated individual information, then analysis module 305 returns to step 604 and repeats the process. For example, an infected individual may have previously been diagnosed with COVID-19 and quarantined for two weeks. A subsequent visit to the doctor may indicate that the individual is no longer infected. This information may be populated back into the system such that analysis of the updated information no longer includes the individual since she is no longer at-risk. This will ultimately affect the health alerts and notifications that are sent by the analysis generator 305A.

The analysis module 305 may also determine there is no updated individual information at step 610, in which case the process proceed to step 612. At step 612, the analysis module 305 determines if a risk has been found from the analysis performed in step 608. If the analysis module 305 determines a risk has been found at step 612, the at-risk individuals are identified at step 616. In this case, the analysis from step 608 yields an assessment and a profile of the risk of individuals who have contracted a disease or infection during the event and the individuals who may potentially contract the disease or infection during the event at the community, regional, and global level based on contact with the at-risk individual. In traditional systems, the names of the at-risk individuals and a way of contacting the at-risk individuals may be presented to health officials. However, to preserve privacy and maintain the anonymity of the individuals and their private data, the event-specific tokens are used to identify the at-risk individuals as having attended the specific event without revealing any of the individual private information or data, including name. If at step 612 no risk is found, then the analysis module 305 terminates processing at step 614.

Figure 7:
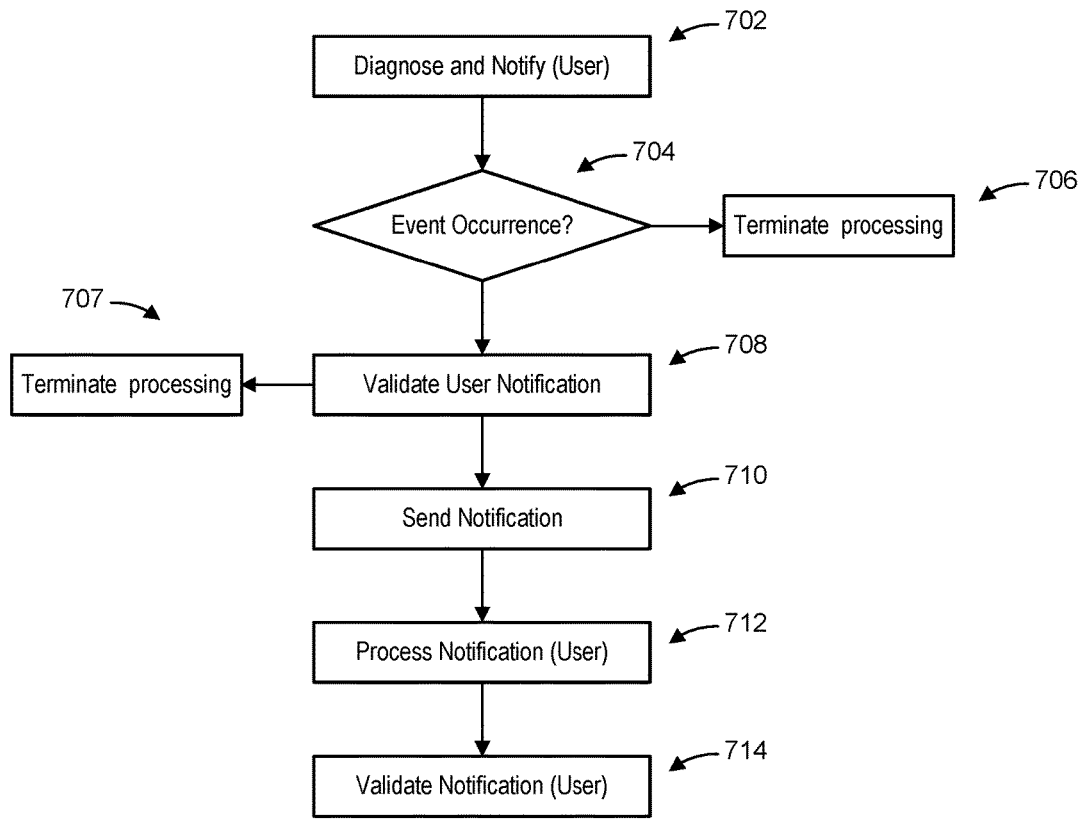
FIG. 7 illustrates a flow diagram for notification propagation for contact tracing in accordance with one example embodiment.

FIG. 7 illustrates a flow diagram for notification propagation for contact tracing in accordance with one example embodiment. The process describes the steps that occur upon an individual or user being diagnosed with a disease or infection, and the steps taken to notify users and health systems, as well as validation of those notifications. In embodiments, the flow diagram may be computer-implemented methods performed, at least partly, by hardware and/or software components illustrated in the various figures and as described herein. In one embodiment, the disclosed process may be performed by the system and components in FIGS. 1, 2 and 6. In one embodiment, software components executed by one or more processors, such as processing unit 914, performs at least a portion of the process. For purposes of the example that follows, an analysis module (in the platform or the personal monitoring device) implements the process.

When an individual or user is diagnosed with a communicable disease or infection by the analysis module 305 at step 702, a notification is sent from the users personal monitoring device to the health tracking and alert platform 103. The notification may include, for example, an indication that the individual or user has been infected with the disease and a copy of the event-specific token stored in the personal health database 110 that relates to the event attended by the individual. The event-specific token may also include, as discussed above, the signature of the individual so that the facility or venue (and platform 103) may validate the notification. For example, for each event-specific token, the individual creates the signature using the corresponding private key (and the message body in the event token) and sends the signatures together with the notification.

At step 704, the analysis module 305 determines whether an event occurred at a facility or venue. For example, public sensors at a venue detect that multiple individuals have recorded high temperatures. The public sensors, when aggregated with public health data (e.g., several incidents of the flu have been reported within the vicinity of the venue), may alert public health authorities that there is a potential for at-risk individuals that attended the venue. When such event occurrences are detected by the analysis module 305 at step 704, previously generated event-specific tokens 500A stored in the public health database 110 may be used to match the event and send notifications to individuals that attended the venue.

If no event has occurred (been detected) at step 704, processing may be terminated at step 706.

At step 708, the platform 103 validates the notification sent by the individual by comparing the received signature with the signatures stored in the corresponding event-specific token. For example, as explained above, for each event-specific token, the individual creates the signature using the corresponding private key. This signature may be compared using the corresponding public keys stored in the correspond event-specific token of the public health database 109. If a match is found, the process proceeds to step 710. Otherwise, the process terminates at step 707.

At step 710, the platform 103 sends a notification with the matched and verified event-specific tokens (and signatures of the venue) to other users' personal monitoring devices. Upon receipt of the notification from the platform 103, at step 712, the personal monitor device of the individual processes the notification to determine whether there is a match between the event-specific token (sent with the notification) and those stored in the personal health database 110 associated with the individual's personal monitoring device. At step 714, if a match is found, the notification sent from the platform 103 is validated using the signature and an alert or notification of the potential risk of attending the event is sent to the individual's personal monitoring device for display to the user.

Figure 8A:
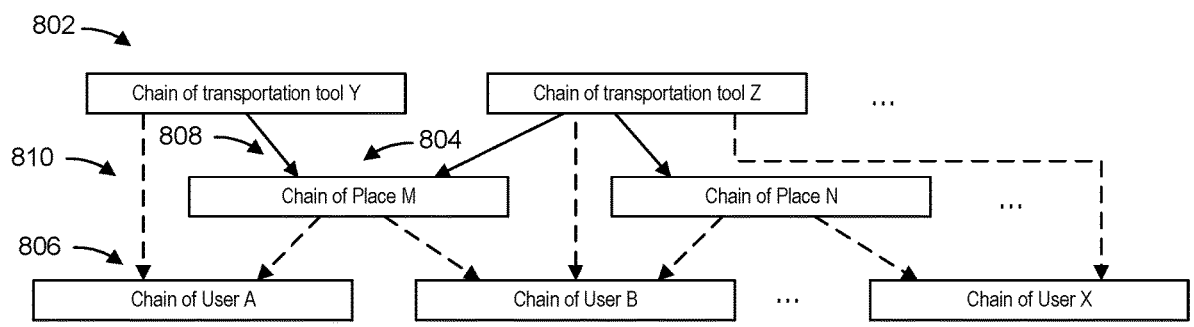

FIGS. 8A and 8B illustrate an example graph structure linking individuals and facilities (or venues) using blockchain technology. Blockchains may be used to decentralize identification as they may provide agreement between devices regarding names and identities that are in current use. A blockchain is a distributed database of identity records that is made up of data structure blocks (or objects), such as those illustrated in FIG. 8B. The term blockchain is not limited to a distributed database of identify records and may also include any one or more of distributed ledger systems including, but not limited to, Hyperledger, Multichain, Keyless Signature Infrastructure, and the like.

In the embodiment of FIG. 8A, the blocks (or node types), represented by blocks 802, 804 and 806, include individual people, public places, transportation vehicles, local communities, etc. Straight edges (or straight lines) 808 represent the interaction between the blocks (e.g., visiting and event token distribution, etc.), and dashed edges 810 (or dashed lines) refer to an implicit linkage. In one embodiment, data collected by the personal and public sensors may be implemented using blockchain technology in order to assist in tracing data. For example, links between blocks (e.g., a link between block 802 and block 804) may be represented using the event-specific tokens generated by the system.

Individual blocks 802, 804 and 806 may be represented by blockchain objects, as shown in FIG. 8B. As individuals move from location to location, events are recorded. For example, in the graph of FIG. 8A, the chain of User A (block 806) is linked to Place M (block 804) and transportation tool Y (block 802), as represented by the straight edge and dashed lines. The individual may use transportation tool Y (e.g., a bus) to travel to Place M. As the individual travels, data is stored in the respective blocks. As shown in FIG. 8B, block 806 (chain of User A) stores the date and time period in which measurements and events are recorded. The events may be recorded to include a timestamp, location and Place ID and health measurements of the individual (including any values or device IDs). Similarly, as the individual comes into contact with other individuals, even-specific tokens may be stored along with an estimated closest distance and an amount of exposure time. Block 804 (chain of Place M) also stores similar information about a particular place visited (in this example, Place M). Block 804 records the date and time period, along with measurements of the individual while at the location (e.g., Place M). Events may be recorded to include events-specific tokens associated with the location, an ID or pseudo ID for Place M, the time the individual entered and left the establishment and health measurements of the individual (including any values or device IDs). Also recorded may be other visitors at Place M that are in close contact with the individual. The "other" visitors may be identified using a pseudo ID so as to protect identify, along with the estimated closest distance and amount of time in contact. Likewise, the transportation tool Y may have event information stored in block 802. Block 802 records the date and time period, and also records events that occur during transportation, such as recording of an individual's health measurements and a traveling trajectory (e.g., the path of travel during transportation), including the location/place ID and a timestamp. Events may be recorded to include an event-specific token, user ID, timestamp of entering and leaving a venue, health measurements (including values and device ID). Also included may be information about other individuals (other passengers) in close contact with the individual while using transportation. Such information may be recorded as a user ID or pseudo user ID, estimate closest distance to the individual and the amount of time of duration or exposure.

Figure 9:
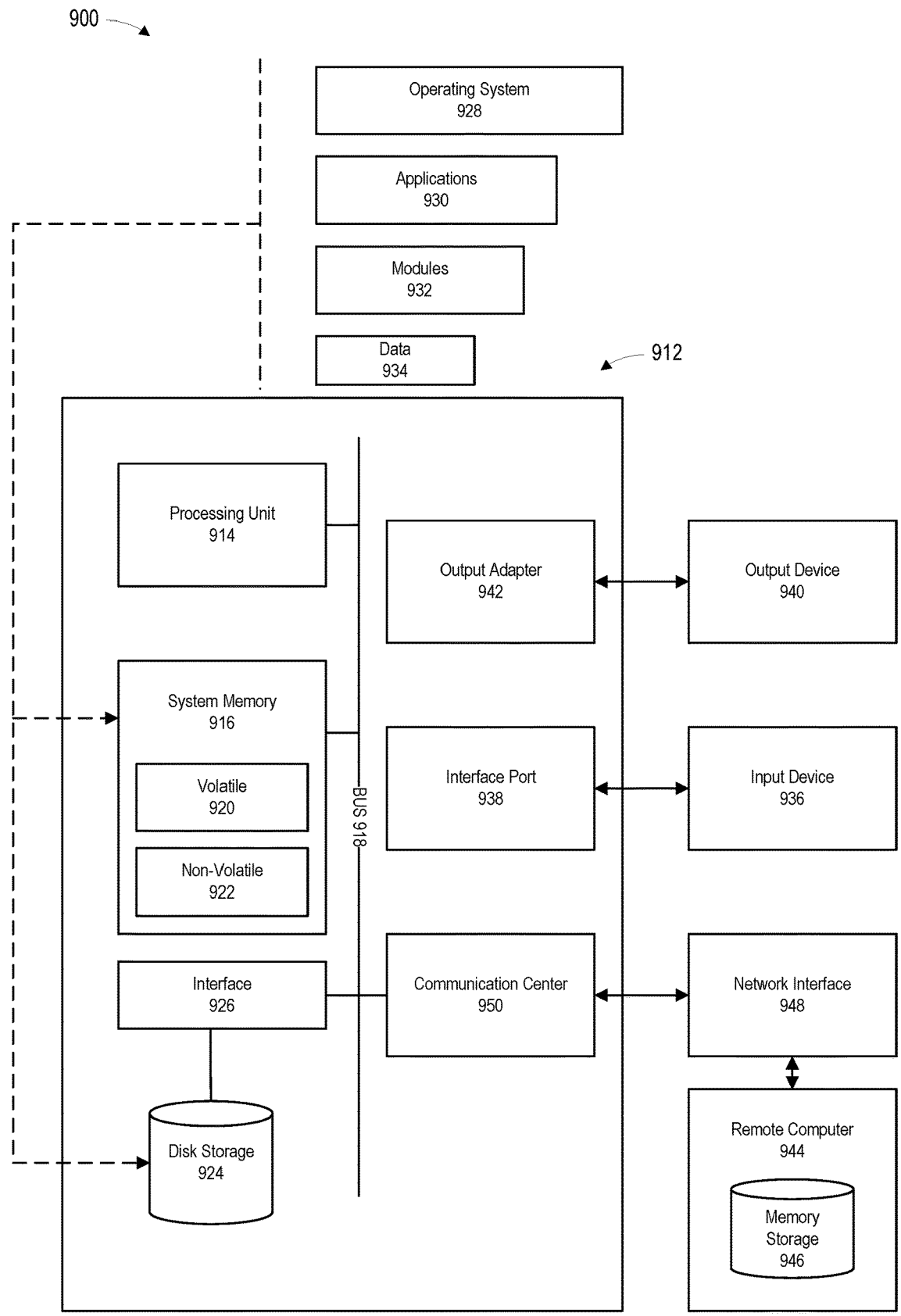
FIG. 9 shows an example embodiment of a computing system for implementing embodiments of the disclosure.

FIG. 9 shows an example embodiment of a computing system for implementing embodiments of the disclosure. A suitable operating environment 900 for implementing various aspects of this disclosure can include a computer (or mobile device) 912. The computer 912 can also include a processing unit 914, a system memory 916, and a system bus 918. The system bus 918 can operably couple system components including, but not limited to, the system memory 916 to the processing unit 914. The processing unit 914 can be any of various available processors. Dual microprocessors and other multiprocessor architectures also can be employed as the processing unit 914. The system bus 918 can be any of several types of bus structures including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire, and Small Computer Systems Interface (SCSI). The system memory 916 can also include volatile memory 920 and nonvolatile memory 922. The basic input/output system (BIOS), containing the basic routines to transfer information between elements within the computer 912, such as during start-up, can be stored in nonvolatile memory 922. By way of illustration, and not limitation, nonvolatile memory 922 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 920 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 912 can also include removable/non-removable, volatile/non-volatile computer storage media. FIG. 9 illustrates, for example, a disk storage 924. Disk storage 924 can also include, but is not limited to, devices like a magnetic disk drive, floppy disk drive, tape drive, Jaz drive, Zip drive, LS-100 drive, flash memory card, or memory stick. The disk storage 924 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 924 to the system bus 918, a removable or non-removable interface can be used, such as interface 926. FIG. 9 also depicts software that can act as an intermediary between users and the basic computer resources described in the suitable operating environment 900. Such software can also include, for example, an operating system 928. Operating system 928, which can be stored on disk storage 924, acts to control and allocate resources of the computer 912. System applications 930 can take advantage of the management of resources by operating system 928 through program modules 932 and program data 934, e.g., stored either in system memory 916 or on disk storage 924. It is to be appreciated that this disclosure can be implemented with various operating systems or combinations of operating systems. A user enters commands or information into the computer 912 through one or more input devices 936. Input devices 936 can include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices can connect to the processing unit 914 through the system bus 918 via one or more interface ports 938. The one or more Interface ports 938 can include, for example, a serial port, a parallel port, a game port, and a universal serial bus (USB). One or more output devices 940 can use some of the same type of ports as input device 936. Thus, for example, a USB port can be used to provide input to computer 912, and to output information from computer 912 to an output device 940. Output adapter 942 can be provided to illustrate that there are some output devices 940 like monitors, speakers, and printers, among other output devices 940, which require special adapters. The output adapters 942 can include, by way of illustration and not limitation, video and sound cards that provide a means of connection between the output device 940 and the system bus 918. It should be noted that other devices and/or systems of devices provide both input and output capabilities such as one or more remote computers 944.

Computer 912 can operate in a networked environment using logical connections to one or more remote computers, such as remote computer 944. The remote computer 944 can be a computer, a server, a router, a network PC, a workstation, a microprocessor based appliance, a peer device or other common network node and the like, and typically can also include many or all of the elements described relative to computer 912. For purposes of brevity, only a memory storage device 946 is illustrated with remote computer 944. Remote computer 944 can be logically connected to computer 912 through a network interface 948 and then physically connected via communication connection 950. Further, operation can be distributed across multiple (local and remote) systems. Network interface 948 can encompass wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). One or more communication connections 950 refers to the hardware/software employed to connect the network interface 948 to the system bus 918. While communication connection 950 is shown for illustrative clarity inside computer 912, it can also be external to computer 912. The hardware/software for connection to the network interface 948 can also include, for exemplary purposes only, internal and external technologies such as, modems including regular telephone grade modems, cable modems and DSL modems, ISDN adapters, and Ethernet cards.

It is understood that the present subject matter may be embodied in many different forms and should not be construed as being limited to the embodiments set forth herein. Rather, these embodiments are provided so that this subject matter will be thorough and complete and will fully convey the disclosure to those skilled in the art. Indeed, the subject matter is intended to cover alternatives, modifications and equivalents of these embodiments, which are included within the scope and spirit of the subject matter as defined by the appended claims. Furthermore, in the following detailed description of the present subject matter, numerous specific details are set forth in order to provide a thorough understanding of the present subject matter. However, it will be clear to those of ordinary skill in the art that the present subject matter may be practiced without such specific details.

Aspects of the present disclosure are described herein with reference to flowchart illustrations and/or block diagrams of methods, apparatuses (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

The computer-readable non-transitory media includes all types of computer readable media, including magnetic storage media, optical storage media, and solid state storage media and specifically excludes signals. It should be understood that the software can be installed in and sold with the device. Alternatively the software can be obtained and loaded into the device, including obtaining the software via a disc medium or from any manner of network or distribution system, including, for example, from a server owned by the software creator or from a server not owned but used by the software creator. The software can be stored on a server for distribution over the Internet, for example.

Computer-readable storage media (medium) exclude (excludes) propagated signals per se, can be accessed by a computer and/or processor(s), and include volatile and non-volatile internal and/or external media that is removable and/or non-removable. For the computer, the various types of storage media accommodate the storage of data in any suitable digital format. It should be appreciated by those skilled in the art that other types of computer readable medium can be employed such as zip drives, solid state drives, magnetic tape, flash memory cards, flash drives, cartridges, and the like, for storing computer executable instructions for performing the novel methods (acts) of the disclosed architecture.

The terminology used herein is for the purpose of describing particular aspects only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain the principles of the disclosure and the practical application, and to enable others of ordinary skill in the art to understand the disclosure with various modifications as are suited to the particular use contemplated.

For purposes of this document, each process associated with the disclosed technology may be performed continuously and by one or more computing devices. Each step in a process may be performed by the same or different computing devices as those used in other steps, and each step need not necessarily be performed by a single computing device.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer-implemented method for managing data in a network, comprising:
    collecting data of an event, at a platform having one or more processors, of one or more users from a plurality of sensors located in the network, the sensors including personal monitoring devices and public monitoring devices;
    generating, by the one or more processors of the platform, an event-specific token corresponding to the event attended by the one or more users, the event-specific token including event-specific signatures about the one or more users attending the event;
    sending public data, by the platform via the network, for storage to a public storage as an aggregation of the collected data of the one or more users, the public data of the one or more users collected using the public monitoring devices and tagged with the event-specific token;
    statistically analyzing the public data, by the one or more processors of the platform, collected from the plurality of sensors at the event to track interactions and assessing risks of the one or more user's potential infection of a communicable disease based on relationships between locations and times in the public data, and reports of the communicable disease at the event; and
    sending an advisory alert, by the platform via the network, to the one or more users personal monitoring devices based on a result of the statistical analysis to warn the one or more users of a level of risk of harm based on attendance of the event, the event-specific token analyzed to identify a relevance of the advisory alert to each of the one or more users.

2. The computer-implemented method of claim 1, further comprising:
    receiving, via the network, personalized data of each of the one or more users from a corresponding private storage, the personalized data of each of the one or more users collected using the plurality of sensors and tagged with the event-specific token, wherein
    the public data includes the personalized data for the statistical analysis when the one or more users authorize sharing the corresponding personalized data, the personalized data maintaining the anonymity of the one or more users in the public storage by removing user identities and matching the event-specific token of the personalized data with the event-specific token of the public data.

3. The computer-implemented method of claim 2, wherein the aggregation includes clustering the aggregated public data and the personalized data to identify clusters of data grouped according to defined categories of information.

4. The computer-implemented method of claim 3, wherein the aggregated public data and the personalized data include the collected data that satisfies one or more conditions or thresholds.

5. The computer-implemented method of claim 2, further comprising:
receiving, via the network, a notification from the personal monitoring device of one of the users previously in attendance of the event that indicates the user has been infected with the communicable disease, the notification including a copy of the event-specific token and an event-specific signature from the one or more users; and
validating, by the one or more processors of the platform, the notification sent by the personal monitoring device by comparing the event-specific signature of the one or more users to signatures of the one or more users stored in the public storage.

6. The computer-implemented method of claim 1, wherein statistical analysis by the one or more processors of the platform comprises one or more of
measuring how many of the one or more users in attendance at the event have been in physical proximity to one another;
determining how many of the one or more users are infected by a same communicable disease; and
predicting the spread of the communicable disease based on transportation and mobility patterns and restrictions placed on the transportation and mobility of the one or more users subsequent to attendance at the event.

7. The computer-implemented method of claim 2, further comprising
distributing, by the platform, the event-specific token to the personal monitoring device and the public monitoring devices in the network, wherein
the event-specific token distributed to the personal monitoring device includes an event hosting facility identifier, a device identifier, a time stamp, an event identifier, a number of the one or more users, the collected data from the plurality of sensors, signatures of the event hosting facility and an event-specific user key, and
the event-specific token distributed to the public monitoring device includes the event hosting facility identifier, the device identifier as the anonymous identifying information, the time stamp, the event identifier, the number of the one or more users, the collected data from the plurality of sensors, the event-specific signatures of the one or more users and an event hosting facility key.

8. The computer-implemented method of claim 7, further comprising
exchanging, by the platform, the signature of the one or more users with the signature of the event hosting facility during distribution of the event-specific token to the personalize monitoring device and the public monitoring device, wherein
the signature of the one or more users is generated using the user key, and
the signature of the event hosting facility is generated using the event hosting facility key.

9. The computer-implemented method of claim 8, further comprising
receiving, by the platform, a new signature of the one or more users generated by the personal monitoring device, the new signature generated using a newly generated key; and
updating, by the platform, the event-specific token of the public data with the new signature.

10. The computer-implemented method of claim 7, wherein the event-specific token distributed to the personal monitoring device of the one or more users includes the signature of the event hosting facility to validate the event-specific token upon receipt of the advisory alert.

11. The computer-implemented method of claim 1, wherein the collected data is tracing data used to trace the one or more users in attendance at the event.

12. The computer-implemented method of claim 1, wherein the collected data is stored as a hierarchical graph structure linking, via the event-specific tokens, groups of the one or more users based on the clustering of the aggregated public data and the personalized data.

13. An apparatus for managing data in a network, comprising:
a non-transitory memory storage comprising instructions; and
one or more processors in communication with the memory, wherein the one or more processors execute the instructions to:
collect data of an event, via the network, of one or more users from a plurality of sensors located in the network, the sensors including personal monitoring devices and public monitoring devices;
generate an event-specific token corresponding to the event attended by the one or more users, the event-specific token including event-specific signatures about the one or more users attending the event;
send public data, via the network, for storage to a public storage as an aggregation of the collected data of the one or more users, the public data of the one or more users collected using the public monitoring devices and tagged with the event-specific token;
statistically analyze the public data collected from the plurality of sensors at the event to track interactions and assess risks of the one or more user's potential infection of a communicable disease based on relationships between locations and times in the public data, and reports of the communicable disease at the event; and
send an advisory alert, via the network, to the one or more users personal monitoring device based on a result of the statistical analysis to warn the one or more users of a level of risk of harm based on attendance of the event, the event-specific token analyzed to identify a relevance of the advisory alert to each of the one or more users.

14. The apparatus of claim 13, wherein the one or more processors further execute the instructions to:
receive, via the network, personalized data of each of the one or more users from a corresponding private storage, the personalized data of each of the one or more users collected using the plurality of sensors and tagged with the event-specific token, and
the public data includes the personalized data for the statistical analysis when the one or more users authorize sharing the corresponding personalized data, the personalized data maintaining the anonymity of the one or more users in the public storage by removing user identities and matching the event-specific token of the personalized data with the event-specific token of the public data.

15. The apparatus of claim 14, wherein the aggregation includes clustering the aggregated public data and the personalized data to identify clusters of data grouped according to defined categories of information.

16. The apparatus of claim 14, wherein the one or more processors further execute the instructions to:
receive, via the network, a notification from the personal monitoring device of one of the users previously in attendance of the event that indicates the user has been infected with the communicable disease, the notification including a copy of the event-specific token and an event-specific signature from the one or more users; and
validate the notification sent by the personal monitoring device by comparing the event-specific signature of the one or more users to signatures of the one or more users stored in the public storage.

17. The apparatus of claim 13, wherein statistical analysis comprises one or more of the one or more processors further executing the instructions to:
measure how many of the one or more users in attendance at the event have been in close physical proximity to one another;
determine how many of the one or more users are infected by a same communicable disease; and
predict the spread of the communicable disease based on transportation and mobility patterns and restrictions placed on the transportation and mobility of the one or more users subsequent to attendance at the event.

18. The apparatus of claim 14, wherein the one or more processors further execute the instructions to:
distribute the event-specific token to the personal monitoring device and the public monitoring devices in the network,
the event-specific token distributed to the personal monitoring device includes an event hosting facility identifier, a device identifier, a time stamp, an event identifier, a number of the one or more users, the collected data from the plurality of sensors, signatures of the event hosting facility and an event-specific user key, and
the event-specific token distributed to the public monitoring device includes the event hosting facility identifier, the device identifier as the anonymous identifying information, the time stamp, the event identifier, the number of the one or more users, the collected data from the plurality of sensors, the event-specific signatures of the one or more users and an event hosting facility key.

19. The apparatus of claim 18, wherein
the one or more processors further execute the instructions to exchange the signature of the one or more users with the signature of the event hosting facility during distribution of the event-specific token to the personalize monitoring device and the public monitoring device,
the signature of the one or more users is generated using the user key, and
the signature of the event hosting facility is generated using the event hosting facility key.

20. A non-transitory computer-readable medium storing computer instructions for managing data in a network, that when executed by one or more processors, cause the one or more processors to perform the steps of:
collecting data of an event of one or more users from a plurality of sensors located in the network, the sensors including personal monitoring devices and public monitoring devices;
generating an event-specific token corresponding to the event attended by the one or more users, the event-specific token including event-specific signatures about the one or more users attending the event;
sending public data, via the network, for storage to a public storage as an aggregation of the collected data of the one or more users, the public data of the one or more users collected using the public monitoring devices and tagged with the event-specific token;
statistically analyzing the public data collected from the plurality of sensors at the event to track interactions and assess risks of the one or more user's potential infection of a communicable disease based on relationships between locations and times in the public data, and reports of the communicable disease detected at the event; and
sending an advisory alert, via the network, to the one or more users personal monitoring device based on a result of the statistical analysis to warn the one or more users of a level of risk of harm based on attendance of the event, the event-specific token analyzed to identify a relevance of the advisory alert to each of the one or more users.

* * * * *